(12) United States Patent
Polei

(10) Patent No.: US 8,347,517 B2
(45) Date of Patent: Jan. 8, 2013

(54) MEASURING DEVICE FOR THE DETERMINATION OF SEVERAL PARAMETERS DURING THE PRODUCTION OF TOTAL DENTAL PROSTHESES

(75) Inventor: Andreas Polei, Lalling (DE)

(73) Assignee: Heraeus Kulzer GmbH, Hanau (DE)

( * ) Notice: Subject to any disclaimer, the term of this patent is extended or adjusted under 35 U.S.C. 154(b) by 122 days.

(21) Appl. No.: 12/721,621

(22) Filed: Mar. 11, 2010

(65) Prior Publication Data

US 2010/0229413 A1  Sep. 16, 2010

(30) Foreign Application Priority Data

Mar. 13, 2009 (DE) .......................... 10 2009 012 678
Jul. 15, 2009 (DE) .......................... 10 2009 033 495

(51) Int. Cl.
*A61C 19/04* (2006.01)
*G01B 3/04* (2006.01)
*G01B 3/56* (2006.01)

(52) U.S. Cl. ................. 33/514; 33/515; 33/471; 433/72

(58) Field of Classification Search ............... 33/1 B, 33/1 C, 512, 513, 514, 561.2, 561.3, 563, 33/565, 566, 465, 471; 433/72, 73; 600/589, 600/590; D10/62, 64
See application file for complete search history.

(56) References Cited

U.S. PATENT DOCUMENTS

| | | | | |
|---|---|---|---|---|
| 1,800,714 A * | 4/1931 | Clapp | ............. | 33/1 R |
| D166,905 S * | 6/1952 | Coates | ............. | D10/62 |
| 2,614,329 A * | 10/1952 | Almorth | ............. | 33/484 |
| 3,474,538 A * | 10/1969 | Kirkegaard | ............. | 33/1 A |
| 4,352,663 A * | 10/1982 | Lee | ............. | 433/73 |
| 4,449,929 A * | 5/1984 | Reese | ............. | 433/56 |
| 4,630,375 A * | 12/1986 | Spolyar | ............. | 33/1 B |
| 4,797,096 A * | 1/1989 | Ito et al. | ............. | 433/26 |
| 5,174,037 A * | 12/1992 | Curtin | ............. | 33/512 |
| 5,497,558 A * | 3/1996 | Wagner | ............. | 33/27.03 |
| 5,678,317 A * | 10/1997 | Stefanakos | ............. | 33/512 |
| 5,950,320 A * | 9/1999 | Dorsey | ............. | 33/512 |
| 6,213,959 B1 * | 4/2001 | Kushida | ............. | 600/587 |
| 6,978,550 B2 * | 12/2005 | Xieh | ............. | 33/27.02 |
| 7,954,251 B2 * | 6/2011 | Nunes et al. | ............. | 33/514 |
| 8,127,459 B2 * | 3/2012 | Nunes et al. | ............. | 33/514 |
| 2004/0107592 A1 * | 6/2004 | Matlis | ............. | 33/512 |

FOREIGN PATENT DOCUMENTS

| | | | |
|---|---|---|---|
| EP | 2228033 A1 * | 9/2010 | |
| JP | 3150439 U * | 5/2009 | |
| SU | 1380742 A * | 3/1988 | |

* cited by examiner

*Primary Examiner* — R. A. Smith
(74) *Attorney, Agent, or Firm* — Norris McLaughlin & Marcus, P.A.

(57) ABSTRACT

The invention relates to a measuring device of flexible material for the determination of parameters for the production of dental prostheses which combines different functions, including protractor, spacing template, ruler and an option of utilizing a compass-formed modulus shear measuring module to facilitate shearing.

3 Claims, 1 Drawing Sheet

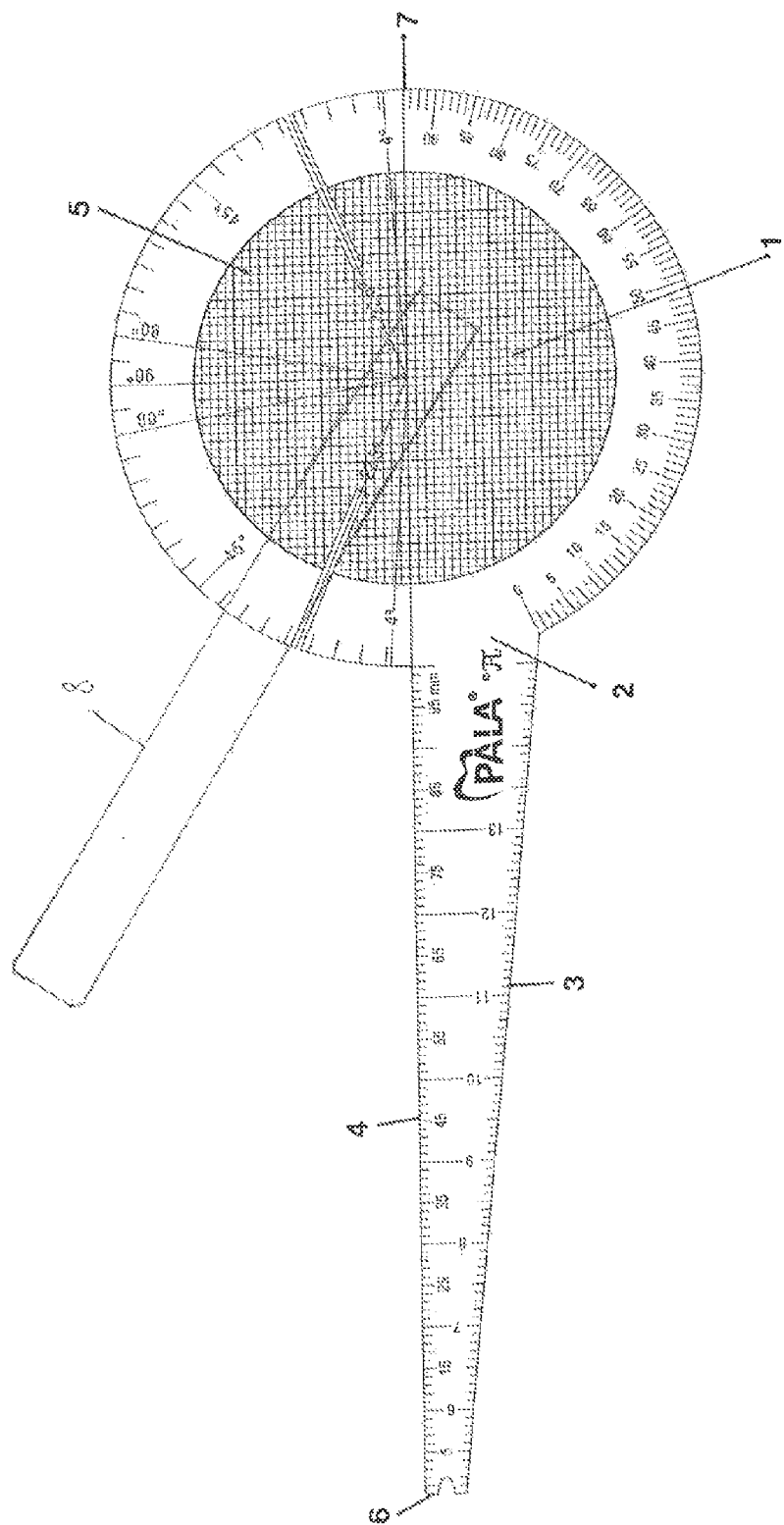

MEASURING DEVICE FOR THE DETERMINATION OF SEVERAL PARAMETERS DURING THE PRODUCTION OF TOTAL DENTAL PROSTHESES

BACKGROUND OF THE INVENTION

During the production of dental prostheses, the dental technician obtains an impression of the oral cavity and surroundings, usually of the toothless of partially anodont jaw. A plaster cast is prepared therefrom. This master cast is used for making one or several working casts. According to the conventional method, the artificial teeth are set in wax on the working cast and the wax is later replaced by synthetic prosthetic base material.

To be able to select and set the artificial teeth, the dentist and dental technician need to take various measurement parameters from the patient and from the master cast. At present, this is done by means of different items of assistive equipment which ought to be in existence at the place of work. These include the following commercially available equipments:

A Papilla Meter is utilized for the determination of the length of the upper lip, as disclosed by Horst Gründler in "Die Totalprothese IV". Grundwissen für Zahntechniker ("The total prosthesis IV", Basic knowledge for the dental technician), Vol. 4, p. 71, Neuer Merkur Verlag; edition: 2. 2004. One of the manufactures producing a Papilla Meter is Candulor). The instrument is used for the determination of measurements unique to the lip closure line in conjunction with the length of the upper lip. The length of the front teeth is dependent upon the lip closure line. The lip length is first measured which enables determining the length of the front teeth.

The same publication discloses an Alameter, see Horst Gründler, p. 70. The Alameter is used for determining the tooth shape. Candulor, also produces the Alameter. The Alameter serves as assistive equipment for assessing the matching tooth shape of the patient by the dentist. After measuring the width of the nose, the approximate width of the tooth shape which suits the face of the patient is calculated. This contributes to a harmonious image of the patient with his/her tooth replacement.

Also knows are transparent measuring grids, usually in the shape of a circular disk (part of a diagnostic tools according to Korkhaus) for determining symmetries and for measuring.

Also used is a set square for finding symmetries and taking pertinent measures.

There are several angle gauges, i.e. for determining critical measurements, such as
 for finding the stop line=22.5°,
 for indicating the cross-bite<=80° (interalveolar connecting line, jaw ridge connecting line),
 as perpendicular to the chewing surface=90°,
 in addition=45°,
 finally, as a reference to the oral inclination of the lower jaw side teeth when setting the premium teeth in accordance with TiF=4°.

Also, a flexible ruler is used for measuring lengths/distances, front dental arch lengths etc. (max. 100 mm).

A sliding gauge is used for measuring single tooth edentulous spaces within a range of 3.2 mm (⅔ of the smallest tooth width) and 13.0 mm, with an accuracy of ¹⁄₁₀ mm.

In certain cases, determination devices known to the expert such as Merz Artegral 9° or Integral 6° have also proved successful.

In view of this described diversity, the invention provides a measuring instrument simple to handle and yet capable of providing multiple measuring parameter.

BRIEF SUMMARY OF THE INVENTION

The invention relates to a measuring device as claimed and shown in the figure. The measuring device is made of transparent flexible material and includes a circular section with a diameter which relates to the area spanning the distance between the outside surfaces of the molars of the right and the left side of the human jaw. Such circular section is connected to form a single section with an interproximal gauge rule, tapering in a distal manner extending from the circular section and having two straight longitudinal sides, each being provided with a graduated scale for measuring the length on a metric or inch-graduated scale or measuring the distance of tooth gaps with distance indications between the two longitudinal sides at corresponding locations. An interproximal measurement is generally accomplished between the proximal surfaces of adjoining teeth.

Further, the extension of one longitudinal side divides the circular part into two halves in form of a visible straight line. One of the halves represents a semi-circular protractor with given angle measurements of 22.5°, 80° und 90° as straight lines running radially from the centre to the circumference of the circular part.

The protractor takes on the role usually carried out by the set square described above. A horizontal base line is used to adjust the table level basically like a spirit level. This horizontal base line is important for all angle references on the measuring device.

The interproximal gauge can be provided with a concave recess at the tip for measuring soft parts.

The measuring device is suitable for the determination of all distances and angles required for cast analysis.

BRIEF DESCRIPTION OF THE SEVERAL VIEWS OF THE DRAWING(S)

FIG. 1 illustrates the device of the invention.

DETAILED DESCRIPTION OF THE INVENTION

The measuring device is made of flexible material and may also be transparent or opaque. The device includes a circular section 1, having a diameter which approximates the distance between the outside surfaces of the molars of the right and the left human jaw. The circular section forms a single piece device with an interproximal gauge rule 2, which tapers in a distal manner from the circular section 1 and having two straight longitudinal sides 3 and 4. Each side includes a graduated scale. The scale of side 3 measures any length with either a metric or an inch-based graduated scale. The scale of side 4 measures the distance of tooth gaps with distance indications between the two longitudinal sides at corresponding locations. The extension of one longitudinal side divides the circular part into two halves by a visible straight line. One of the halves represents a semi-circular protractor 5 with predetermined, given angle measurements of 22.5°, 80° und 90° as straight lines running radially from the centre to the circumference of the circular part.

The protractor takes on the role usually carried out by the set square described above in the background section. A horizontal base line 7 is used to adjust the table level, basically like a spirit level. This horizontal base line is important for all angle references on the measuring device.

Relationships of Measurements a) gap widths:
  The gap width of individual teeth is determined according to well known devices.
b) Edentulous spaces:
  The flexible linear graduated scale allows the metric determination of the edentulous space.
c) Side tooth width (distance from eye tooth to stop line):
  The distance between the eye tooth line and the stop line which is to correspond to the side replacement tooth width is measured with the linear graduated scale.
d) Front dental arch
  Flexible linear graduated scale;
e) Tooth length (distance between the wax edge and the aesthetic template smile line):
  The edge of the aesthetic template corresponds to the visible portion of the replacement front teeth with the lip being relaxed. The smile line corresponds to the baring of the front teeth during soft part movement. The distance between the upper edge of the aesthetic template and the smile line thus gives the length of the replacement teeth so that as little prosthesis plastic as possible is visible on smiling.
f) Front tooth width (distance eye tooth bottom):
  The distance between the two eye teeth lines gives the width of the lower jaw replacement front teeth. The flexible linear portion is used for carrying out the measurement.
g) Intraalveolar distance measured with the linear graduated scale of the gap measuring device on articulated casts with flexible design.
  The distance between the edentulous jaws gives the measure of the side replacement tooth height. It allows the assessment to be made of the use of setting aids such as e.g. Filou-28 from Heraeus, Hanau, DE. The measurement is carried out on the back side of the cast with the grid of the round portion of the alveolometer.
h) 80° Angle für measuring the interalveolar angle on articulated casts.
i) 22.5° angle for measuring the stop line which indicates to the dental technician the distal position from which onwards he/she cannot set any further teeth with dental occlusion.
  The point of intersection of the 22.5° line with the course of the jaw edge transferred on the outside of the cast can be recorded directly by notches in the assistive measuring device.
j) Soft part relationships can be determined by means of the recess on the distal end of the gap measuring device. For this purpose, the recess is placed onto the labial frenulum. Using the linear graduated scale, it is then possible to determine the dimension of the attached gingiva and the lip length. These values are important for assessing the visible portion of the prosthesis plastic.
k) Using the optional device for measuring the modulus of shearing, the width of the nose can be determined directly on the nasal wings of the patient. This measurement is required for selecting the front replacement tooth width.
  Such a modulus 8 of shearing similar to that of a compass is provided by a flexible connection between two measuring shanks in the centre of the round portion 1 which opens up further measuring possibilities (e.g. vertical and/or transverse measurements) and allows the transfer of these measurements to other measuring sites and thus a direct comparison of the measurements (without reading a radial metric graduated scale which may be applied onto the circular circumference).

The measuring device according to the invention can be used both in the dental laboratory for cast analysis and in the dental surgery for rapid verification and cast analysis.

In particular, the following applications are suitable in situations arising in the implant planning stage, when it is necessary to measure the gap width of the patient as well as the gap height for inserting implants into the patient. The height is particularly important for the subsequent provision of the implant with a crown via an insert since a minimum height is required which is dependent on the manufacturer.

The device of the invention, and in particular, the optional devices, facilitates a realistic visualization during the planning of the implantation, and thereby, the invention does contribute to the success of acceptance of the new implants by the patient. The success of a prostheses is accomplished by early envisioning the dental arch in front of an edentulous space by the flexible portion. The device utilises facial and oral asymmetries by measurable visualisation with the aid of a working cast.

The invention claimed is:

1. A measuring device of transparent flexible material for determining parameters characteristic of a person's mouth cavity, jaw and oral configuration for the production of dental prostheses, comprising
  a circular section (1) having a diameter representing the distance between the outside surfaces of the right side and left side molars,
  an interproximal gauge rule (2) forming a first measuring arm;
  the circle section (1) transitions and forms a single section with the interproximal gauge rule (2);
  the interproximal gauge rule (2) tapers distally, starting from the circular section (1) and includes two straight longitudinal sides, forming a first scale and a second scale;
  the first scale represents a graduated scale (3) for measuring length on a graduated scale;
  the second scale (4) represents a graduated scale (4) for measuring the distance of tooth gaps with distance indications between the two longitudinal sides at corresponding locations, the extension of one of the two straight longitudinal sides dividing the circular section into two halves in the form of a visible straight line.

2. The measuring device according to claim 1, wherein the interproximal gauge rule terminates in a tip (6) formed as a concave recess.

3. The measuring device according to claim 1, further comprising
  a second measuring arm (8) pivotably connected centrally in the circular section (1).

* * * * *

UNITED STATES PATENT AND TRADEMARK OFFICE
CERTIFICATE OF CORRECTION

| | | |
|---|---|---|
| PATENT NO. | : 8,347,517 B2 | |
| APPLICATION NO. | : 12/721621 | |
| DATED | : January 8, 2013 | |
| INVENTOR(S) | : Polei | |

It is certified that error appears in the above-identified patent and that said Letters Patent is hereby corrected as shown below:

In the Specification

Column 1, line 3, "toothless of" -- should read -- toothless or --.

Column 1, line 29, "manufactures" -- should read -- manufacturers --.

Signed and Sealed this
Fifth Day of August, 2014

Michelle K. Lee
*Deputy Director of the United States Patent and Trademark Office*